United States Patent [19]
Moore

[11] Patent Number: 5,997,796
[45] Date of Patent: *Dec. 7, 1999

[54] IMPLANT HAVING INTEGRALLY-TEXTURED, HEMOCOMPATIBLE, BLOOD-CONTACTING SURFACES AND METHOD FOR PRODUCING THE SAME

[75] Inventor: Daniel R. Moore, Allegheny, Pa.

[73] Assignee: Vascor, Inc., Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/751,839

[22] Filed: Nov. 18, 1996

Related U.S. Application Data

[63] Continuation of application No. 08/512,301, Aug. 8, 1995, abandoned.

[51] Int. Cl.⁶ .......................... B29C 33/42; B29C 33/52
[52] U.S. Cl. ....................... 264/439; 264/102; 264/221; 264/225; 264/226; 264/227; 264/317; 264/255; 264/571; 264/DIG. 44
[58] Field of Search ................................ 264/227, 221, 264/317, 226, 225, DIG. 44, 440, 439, 102, 571, 255

[56] References Cited

U.S. PATENT DOCUMENTS 3,265,796  8/1966  Rodriguez .
4,016,303  4/1977  Poirier et al. .

(List continued on next page.)

FOREIGN PATENT DOCUMENTS 370292  11/1988  European Pat. Off. .
315814  5/1989   European Pat. Off. .
416846  3/1991   European Pat. Off. .
710468  11/1994  European Pat. Off. .

OTHER PUBLICATIONS

Abstract of Japan vol. 012, No. 434.
Abstract of Japan vol. 013, 315.
"Fabrication and Testing of Flocked Blood Pump Bladders", by Victor Poirier. Thermo Electron Corporation, Waltham, Massachusetts.
"Polyester Fibril Flocked Surface for Blood Pumps", by H. Harasald, A. Field, N. Sato, J. Snow, R. Kiraly and Y. Nose, Trans. Am Soc. Artif. Intern. Organs, vol. XXIX, 1983.
"Development and Testing of Flocking Materials", by M. Szycher, W.F. Bernhard, v. Poirier, C. Franzblau, C.C. Haudenschild, Thermo Electron Corporation, Waltham, Massachusetts, prepared for National Heart, Lung and Blood Institute, Bethesda, MD, Apr. 1979.

*Primary Examiner*—Jan H Silbaugh
*Assistant Examiner*—Suzanne E. Mason
*Attorney, Agent, or Firm*—Buchanan Ingersoll, P.C.

[57] ABSTRACT

An implant having an integrally-textured, hemocompatible blood-contacting surface and a method for producing the same is provided. The implantable device can include a device body having a textured surface and a predefined complex shape, such as a bladder or a generally U-shaped conduit. The device body can be composed of a first device material, and the textured surface can be formed of a second device material on the obverse side of the device. The textured surface can have multiple, blood-compatible structures integrally formed thereon. The structures can be fibrils that are suitable for a generally uniform biological layer to be established thereupon. The method for producing an implantable device can include the steps of fabricating a mold; applying a flock to the mold; introducing a conformable dissoluble material to the mold; removing the dissoluble material from the mold; removing the flock from the dissoluble material using a first solvent thereby creating a dissoluble device form having a form surface having multiple invaginations therein; applying a layer of a selected device material to the dissoluble device form thereby providing a device wall with the structures being integrally formed thereon; and removing the dissoluble device form from the device wall by liquefying the device form, thereby providing the implantable device.

41 Claims, 4 Drawing Sheets

U.S. PATENT DOCUMENTS

| | | |
|---|---|---|
| 4,084,266 | 4/1978 | Poirier et al. . |
| 4,118,806 | 10/1978 | Poirier et al. . |
| 4,312,826 | 1/1982 | Colvin . |
| 4,729,766 | 3/1988 | Bergentz et al. . |
| 4,767,418 | 8/1988 | Deininger et al. . |
| 5,227,576 | 7/1993 | Howard . |
| 5,354,338 | 10/1994 | Ledergerber . |

Fig.1.

STEP 1 Make Mold — Fig.2a.

STEP 2 Apply flock to mold using Electrostatic applicator — Fig.2b.

STEP 3 Cast wax in flocked mold — Fig.2c.

STEP 4 Remove wax form from mold (Flock embedded in surface) — Fig.2d.

STEP 5 Soak wax form in Phenol bath (Phenol dissolves flock) — Fig.2e.

STEP 6 Rinse wax form with water (Many pores in surface of wax) — Fig.2f.

STEP 7 Dip-coat wax form with polyurethane solution — Fig.2g.

STEP 8 Air-dry wax form to remove solvent from polyurethane coating — Fig.2h.

STEP 9 Melt wax and remove from cast polyurethane bladder — Fig.2i.

STEP 10 Integrally-textured polyurethane bladder is dried — Fig.2j.

IMPLANT HAVING INTEGRALLY-TEXTURED, HEMOCOMPATIBLE, BLOOD-CONTACTING SURFACES AND METHOD FOR PRODUCING THE SAME

This application is a continuation of application Ser. No. 08/512,301, filed Aug. 8, 1995, now abandoned.

BACKGROUND OF THE INVENTION

1. Field of the Invention

The present invention relates to devices that are implanted in animals, for example, human beings, and have direct contact with blood.

2. Description of the Prior Art

In certain devices implantable in an animal, such as a human, it is desirable to provide blood-contacting surfaces that are substantially stable and biocompatible. One of the problems that can be encountered in connection with implanted devices is incompatibility of blood-contacting surfaces with the blood to the extent of inducing thrombosis or damage to the blood.

One approach to producing hemocompatible surfaces is to bond polyester fibrils to polyurethane substrates. The bonded fibrils or flocking can create a textured surface that can initiate controlled blood clotting which ultimately can result in a generally stable biological lining. Although a textured surface of polyester flocking can promote formation of a biologic lining, fibers may separate from the substrate and can be washed away in the blood stream to lodge in vital organs such as the brain or spleen.

U.S. Pat. No. 4,016,303 discloses a method for addressing the separation of polyester fibers from blood pump surfaces by over-coating the fibers with polyurethane after bonding the fibers to the polyurethane substrate. However, fiber separation can still occur and implantable devices produced by that method may be unacceptable for particular applications.

Another approach to forming a textured, biocompatible surface can involve forming the fibers as an integral part of the blood-contacting devices, such as a polyurethane blood bag, so that an adhesive bond between fibers and substrate may not be used. By forming the blood bag on a mold that had a surface containing millions of microscopic pores or invaginations, such textured surfaces can be obtained. Using this method, a female mold of the desired device shape can be constructed, typically of brass, and assembled. The female mold can be placed in the tail stock of a lathe and rotated while a custom-built electrostatic applicator is inserted into the mold cavity to apply nylon flock to the mold surface. A thermoset silicone molding compound can be cast into the mold cavity to make a male mold for dip-coating, or solution casting, of the desired substrate material. The nylon fibers can be dissolved from the silicone male mold with a solvent solution such as phenol-methylene chloride to produce a mold that can contain millions of microscopic invaginations which correspond to the dissolved nylon fibers.

A significant limitation of this technique is that it accommodates device configurations of relatively simple shape, primarily axi-symmetric structures such as a cylinder because the electrostatic applicator needs to fit inside the rotating mold assembly. The size of the electrostatic applicator also can impose a practical minimum diameter for the blood bag, which can be dictated by the diameter of the applicator and the air gap between applicator and mold which can prevent electrical arcing. Another limitation of this method can be that the cross-sectional area of the blood bag may not vary significantly because of the difficulty in stretching the polyurethane bag to remove it from the silicone male mold.

What is needed then is an implant having integrally-textured, hemocompatible blood-contacting surfaces, and a method for producing the same, that obviate the aforementioned limitations and disadvantages. Moreover, it is desired to produce such implants having complex shapes.

SUMMARY OF THE INVENTION

The invention herein provides an implant having an integrally-textured, hemocompatible blood-contacting surface and a method for producing the same. Additionally, the implantable device can have a complex shape.

The implantable device can include a device body having a textured surface. The device body can be composed of a first device material, and have a predefined thickness. The textured surface can be formed of a second device material on the obverse side of the device. The textured surface can have multiple, blood-compatible structures integrally formed thereon. The structures can be fibrils that are suitable for a generally uniform biological layer to be established thereupon. The device body can have a predefined complex shape, such as a bladder or a generally U-shaped conduit. Furthermore, the first and second device materials can be the same material, for example, polyurethane.

The method for producing an implantable device can include the steps of fabricating a mold; applying a flock to the mold; introducing a conformable dissoluble material to the mold; removing the dissoluble material from the mold; removing the flock from the dissoluble material using a first solvent thereby creating a dissoluble device form having a form surface with multiple invaginations therein; applying a layer of a selected device material to the dissoluble device form thereby providing a device wall with structures integrally formed thereon; and removing the dissoluble device form from the device wall by liquefying the device form, thereby providing the implantable device.

The flock can be electrostatically attached to the mold and secured to the mold by a suitable adhesive. When the mold is substantially non-conductive, the selected flock attaching technique also can include masking at least a portion of the mold with a conductive tape which is substantially in contact with the adhesive, thereby making the mold electrically conductive. After the conformable dissoluble material is introduced to the mold, both the conformable dissoluble material and the mold at a preselected casting temperature. When the conformable dissoluble material, which can be wax, is introduced to the mold, the flock becomes at least partially embedded therein, and remains so embedded when the dissoluble material is removed from the mold. The flock can be nylon and can be removed from the dissoluble material using a first solvent, such as phenol, yielding the dissoluble device form. The first solvent can be applied in an agitated bath. The selected device material is at least partially dissolved in a third solvent to a first preselected solids content. The layer of selected device material is applied in a manner that causes the material to penetrate the invaginations and create the structures and, thus, the integrally-textured surface.

Applying the flock can include applying a preselected adhesive to at least a portion of the mold and removably imparting the flock to said at least a portion of said mold using a selected flock attaching technique. The dissoluble device form can be removed from the device wall by bathing the device form in a liquefacient which substantially liquefies the dissoluble device form, aiding its removal. Where the conformable dissoluble material is wax, the liquefacient can be water having a temperature greater than the melting point of the wax. Furthermore, residual portions of the dissoluble device form can be removed by bathing the implantable device in a fourth solvent. Once the implantable device has been separated from the device form, the device can be dried at a preselected drying temperature for a preselected drying time.

The selected device material can be a polyurethane such as polycarbonate diisocyanate polyurethane and the third solvent can be a polyurethane solvent, including dimethylacetamide, dimethylformamide, tetrahydrafuran, and 1,4-dioxane. With the polyurethane so dissolved, applying the layer of selected device material can further include dip-coating the dissoluble device form with a coating of device material, and applying a preselected vacuum to the dissoluble device form and the device material such that air entrapped in the invaginations is substantially evacuated therefrom. The vacuum can be applied repeatedly. The layer of device material can be composed of multiple coatings providing the device wall with a predefined thickness, with selected coatings being dried before subsequent coatings are applied.

The implantable device additionally can be finished after the removal of the dissoluble device form by rinsing the implantable device in an n-alcohol, thereby removing residual solvents; rinsing the implantable device in distilled water, thereby removing residual n-alcohol; and drying the device at a preselected drying temperature for a preselected drying time.

DETAILED DESCRIPTION OF THE PREFERRED EMBODIMENTS

Figure 1:
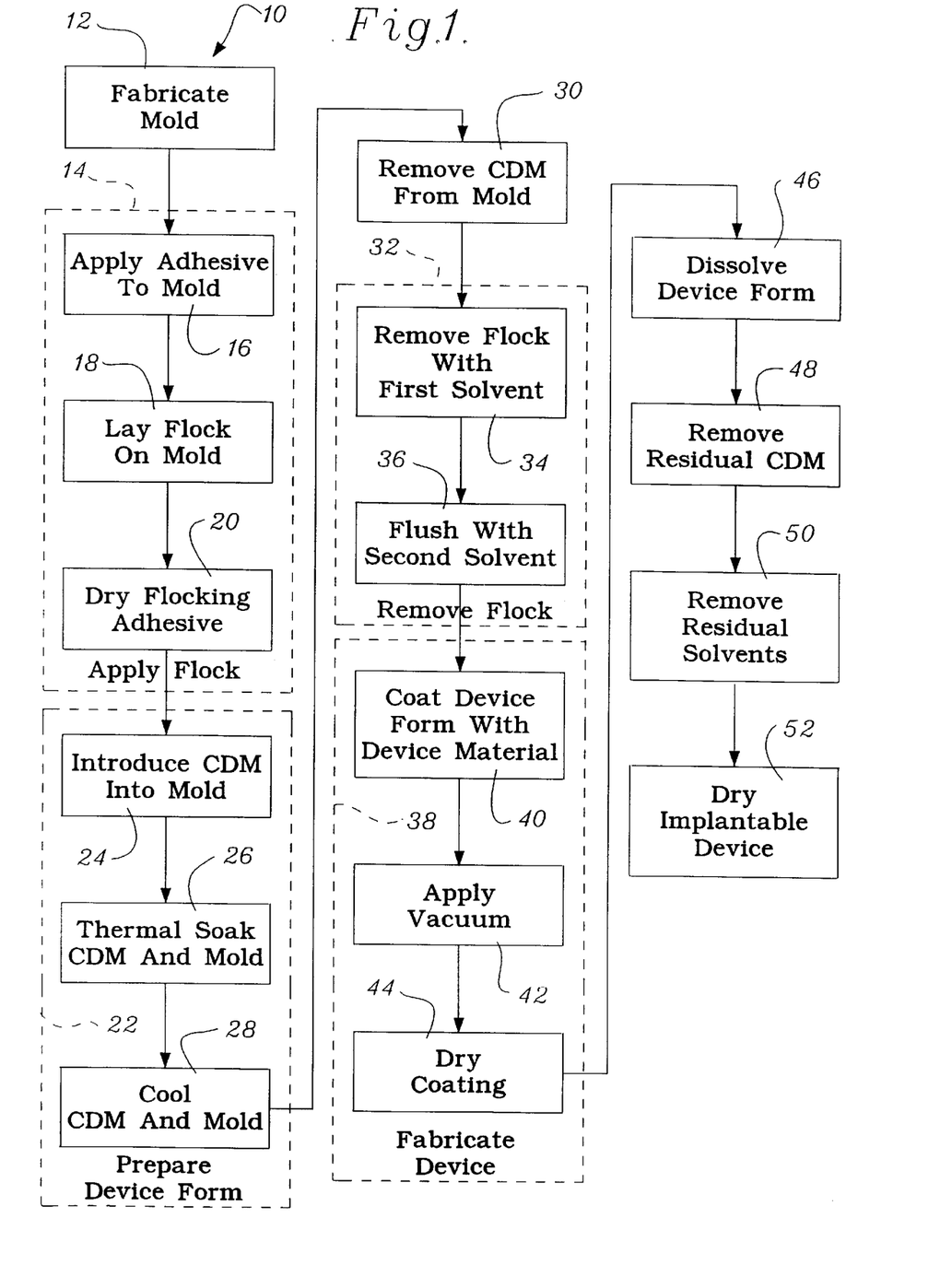
FIG. 1 is a flow diagram which illustrates an embodiment of the process for producing integrally-textured devices according to the invention herein.

As indicated in FIG. 1, process 10 can begin by fabricating a mold having a predefined shape, step 12, to produce a dissoluble device form suitable for dip-coating. Generally, a portion of the mold can have a configuration and dimensions similar to those of a portion of the device to be fabricated. The mold can be made of a suitable molding material which can be rigid, such as metal, or at least partially pliant, such as epoxy or silicone. The mold can be single-sided so that a single-contact-surface device, such as a diaphragm, can be manufactured therefrom. Alternatively, the mold can be a multi-part mold so that a generally continuous-contact enclosed surface having a complex configuration, such as a blood conduit, bladder, or bag, can be fabricated.

Applying a flock to the mold, step 14, can include applying an adhesive step 16 to at least a portion of the mold to be flocked, and imparting the flock, step 18, to the adhesive-coated portion using a selected flock attaching technique. The adhesive can be formulated to be suitable for use with the selected method of imparting flock to the mold. In general, the adhesive can be such that it has adequate bond strength to adhere the flock to the mold for the casting of the form, yet possess sufficient release properties to facilitate de-tooling of the device form after dip-coating. The adhesive can be applied upon the mold surfaces to a generally uniform thickness, particularly in the vicinity of mold edges, where a parting line can occur. The adhesive thickness and solids content can be adjusted to provide a sufficient adhesive coating in the vicinity of a parting line. The adhesive can be applied using a suitable technique, for example, by dipping, brushing, air spraying, and the like.

When the flocking is imparted electrostatically to the mold surfaces, at least a portion of the mold, including the adhesive-coated surfaces, can be electrically grounded. Where the mold is fabricated from a material that is substantially non-conductive, such as epoxy or silicone, at least a portion of the mold cavity surface can be masked with a conductive tape, such as conductive aluminum tape, prior to the application of the adhesive. When the adhesive is applied, a portion of it can be lapped over the conductive tape so that an adequate electrical ground can be established. The flock can be made of a selected material, for example nylon, that is suitably finished for the selected flock attaching technique. In addition, the flock can be pigment-free. Where the selected flock attaching technique is an electrostatic application, the flock and the mold can be placed into the applicator which has been charged to a electrostatic potential. Flock that adheres to mold surfaces outside of the mold cavity can be removed before the adhesive is dried. Where a multi-part mold is fabricated, selected parts of the mold can be assembled while the adhesive is wet, although the mold also can be assembled after the adhesive has dried. The adhesive can be dried, step 20, by placing the flocked mold in an oven at a preselected drying temperature for a preselected drying time.

After the mold has been flocked at step 10, the method continues by preparing a dissoluble device form, step 22, which includes introducing a conformable dissoluble material (in FIG. 1, "CDM") into the mold, step 24. The conformable dissoluble material can be, for example, a wax, such as paraffin or beeswax. To produce a substantially homogeneous casting, the conformable dissoluble material and the mold can be thermally soaked, step 26, at a preselected casting temperature. In this manner, the dissoluble material essentially engulfs the flock and the flock becomes embedded in the surface of the dissoluble material. The mold and dissoluble material can be cooled, step 28, to a second preselected casting temperature to facilitate removal of the dissoluble material from the mold. When the dissoluble material is removed from the mold, step 30, the flock remains embedded in the dissoluble material surface. Flocking adhesive often releases from the mold cavity, covering at least a portion of the dissoluble material surface. This residual adhesive can be removed, for example, by mechanical peeling.

The method can continue by removing the embedded flock, step 32, from the dissoluble material to produce a dissoluble device form suitable for dip-coating. The flock can be removed by bathing the dissoluble material in a first solvent, step 34, that is suitable for dissolving the flock material. The device form can remain in the bath for a preselected bathing period, for example, about 48 hours, to allow the embedded flock in the dissoluble material surface to be substantially dissolved by the first solvent. The dissoluble device form is preferred to be substantially insoluble in the first solvent. After the flocking is removed, the device form can be removed from the bath and flushed with a second solvent, step 36, to remove the first solvent. Once the flock is removed at step 32, the device form surface can have a plurality, perhaps millions, of invaginations that can correspond to the now-removed flock structures, e.g., fibrils.

The device form can be used to fabricate the implantable device, step 38. In general, the dissoluble device form can be dip-coated with a selected device material, step 40, that is dissolved in a third solvent so that the device form can be suffused with the device material. In general, the choice of solvents and solids content can be selected to produce a dip-coating mixture that can produce substantially uniform, bubble-free coatings which can be easy to handle. The dissoluble device form can be submerged into the dip-coating mixture until the device form surface is wetted. To facilitate the penetration of the device material-solvent mixture into the invaginations on the device form surface, the dip-coating can be conducted in a vacuum chamber, step 42. Furthermore, a preselected vacuum can be drawn and released, preferably repeatedly, so that air entrapped within the invaginations can be evacuated. In this way, structures, such as fibrils, composed of the device material can be formed within the invaginations and an obverse side of the device wall and, hence, the implantable device body, can be formed. The dip-coating mixture and device form can be removed from the vacuum chamber and the device form can be removed from the mixture at a controlled rate. Repeated coatings of the dip-coating mixture can be applied in this way to the reverse side of the device wall until a predetermined wall thickness is achieved. Each coating of device material may be dried, step 44, prior to subsequent coatings. Here, the fibrils produced during the aforementioned dip-coatings, step 40, are essentially integral with the obverse side of the device wall and, hence, the device.

The dissoluble device form can be removed from the implantable device by applying a liquefacient at a preselected liquefaction temperature, step 46, to the device form/implantable device composite structure. The liquefacient can liquefy the dissoluble device form such that most, if not all, of the dissoluble material of which the device form is composed, is removed from the device. Liquefaction can include, for example, melting or dissolving. A fourth solvent may be applied to the device to remove residual dissoluble material, step 48, from the device, including the residual dissoluble material remaining on the fibrils. Both the liquefacient and the fourth solvent may be applied by multiple washings in separate baths, each at a preselected temperature and for a preselected time. Further, the device can be rinsed repeatedly in fifth, and additional, solvents including alcohols and distilled water to purge the device of the residue of previous solvents, step 50. With the device being sufficiently cleaned, the device can be dried at a preselected drying temperature for a preselected drying time, step 52. Because the device form can be dissolved and removed from within the formed device, an implantable device produced according to the invention herein can have an internal, closed, blood-contacting surface, and a complex shape. Therefore, such devices can be a tube, a bladder, or a sac having a structure that can be regular, asymmetric, or tortuous.

Figure 2A:
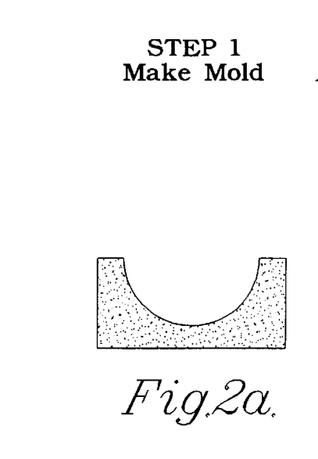
FIGS. 2a–j are diagrammatic representations of the steps in an embodiment of the process for producing integrally-textured devices according to the invention herein.

In one presently preferred embodiment of the method illustrated in FIG. 1 and the description thereof, a blood-compatible, integrally-textured device having a complex shape can be produced using, for example, the steps illustrated by FIGS. 2a–2j. In FIG. 2a, a female mold of epoxy, silicone, or metal is created to produce a device form that will have the desired shape of at least a portion of the article to be made. The mold can be prepared for flocking by the application of a suitable water-based adhesive such as ethyl vinyl acetate, that is formulated for the selected flock attaching technique which, for the embodiment illustrated in FIGS. 2a–2j, is electrostatic flocking. To this end, adhesive solids content can be between about 40% and about 60%, although lower concentrations of solids content may be used. The adhesive is applied in a generally uniform thickness to the mold cavities and to the mold edges where a parting line can occur. An example of an adhesive suitable for electrostatic flocking is a water-based compound of ethyl vinyl acetate, such as S4129 adhesive by American Finish and Chemical Co., Chelsea, Mass.

Figure 2B:
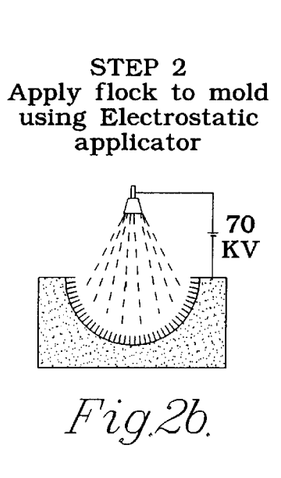

The mold, and particularly the wet adhesive, can be electrically grounded to allow for application of nylon flock to the mold surfaces. If the mold is non-conductive, conductive aluminum tape is used to mask at least a portion of the mold cavity with at least some adhesive being lapped over a portion of the tape to provide an electrical ground. In FIG. 2b, flock is applied to the mold using an electrostatic applicator that is charged up to about 70 kilovolts potential. A suitable electrostatic applicator can be, for example, the DEKOR B electrostatic applicator by Creative Coatings Corporation, Nashua, N.H. Flock application is done via standard techniques to provide uniform coverage on mold surfaces. The nylon flock is pigment-free and finished for electrostatic application. The flocked mold can be dried in an oven at temperatures of between about 40° C. to about 90° C. for between about one hour and about four hours. It is preferred that drying be performed between about 60° C. to about 90° C. for at least one hour.

Figure 2C:
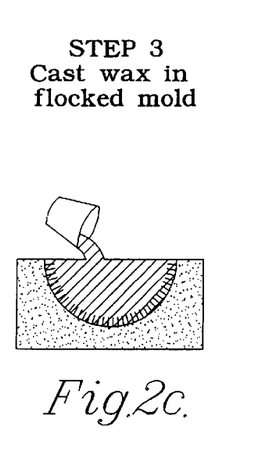
Figure 2D:
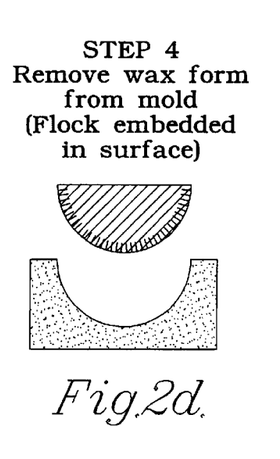
Figure 2E:
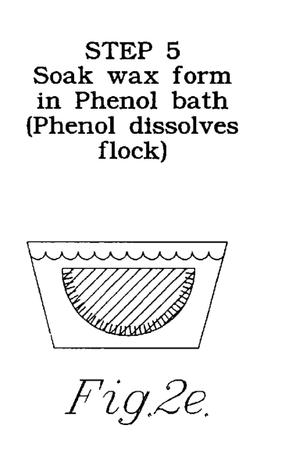
Figures 2F, 2G:
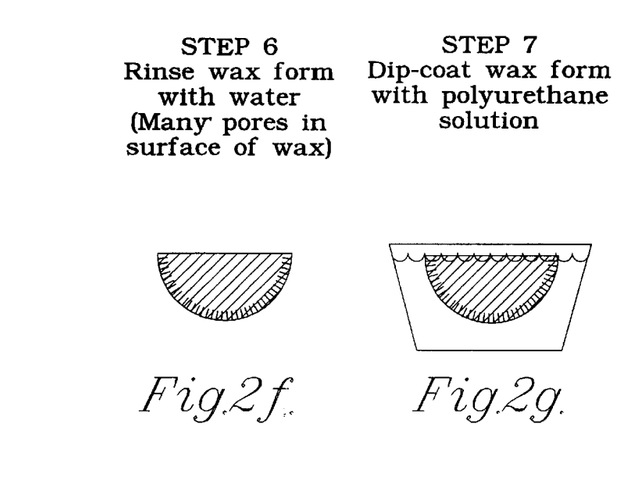
Figure 2H:
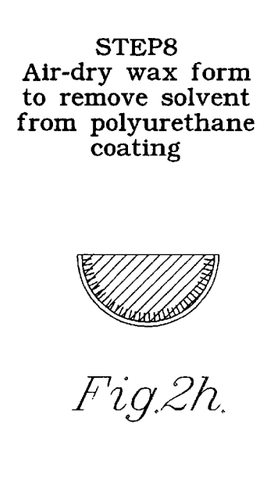

Conformable dissoluble material, for example, melted wax, is cast into the flocked mold cavity in FIG. 2c. The wax can be either paraffin or beeswax. Both the wax and the mold can be thermally soaked at a preselected casting temperature between about 60° C. to about 100° C., as needed, to produce a homogeneous casting. The mold and wax are cooled to about 20° C. before the wax device form is removed from the mold. When the wax form is removed from the mold, nylon flock tends to remain embedded in the device form surface that was proximate to the flocked mold surface. After the wax device form is removed from the mold, in FIG. 2d, the form is placed in a first solvent which can be a stirred bath of a mixture of about 89% phenol and about 11% water, in FIG. 2e. The wax device form can remain in the phenol bath for at least 48 hours to allow the nylon flock that is embedded in the device form surface to be dissolved by the phenol. The wax device form can be removed from the phenol bath and rinsed several times with a suitable second solvent to remove residual phenol, in FIG. 2f. Such a second solvent can be, for example, ethanol, chloroform, acetone, or ether.

In this embodiment, the wax device form can have millions of invaginations in its surface which correspond to the nylon flock fibrils that were dissolved by phenol. The wax device form can be dip-coated with a solution of the selected device material dissolved in a third solvent. In the embodiment illustrated in FIG. 2g, the device material is a polyurethane. Where the selected device material is polycarbonate diisocyanate polyurethane, the third solvent can be dimethylacetamide. However, other solvents such as dimethylformamide, tetrahydrafuran, and 1,4-dioxane also can be used as the third solvent. Although the selected device material can be mixed in the third solvent to a solids content of about 15% by weight, a solids content of between about 1% to about 20% can be used.

The dip-coating of the wax device form can be conducted in a vacuum chamber to provide a means for evacuating the air from the invaginations in the wax device form, so that the polyurethane solution can fill them to produce polyurethane structures, such as fibrils. Both the wax device form and dip-coating solution can be heated to temperatures less than the melting point of the wax. The wax device form can be submerged into the dip-coating solution at a controlled rate until the device form is thoroughly wetted, in FIG. 2g. The dip-coating solution and device form can be placed into a vacuum chamber having a vacuum of between about 5 psia to about 10 psia. The vacuum repeatedly can be drawn and released on the solution and the device form to remove air that may be entrapped in the invaginations in the wax device form and to force polyurethane into the invaginations. In this way, the device wall can be formed with the fibril structures being integrally formed thereon. In general, the obverse side of the device wall, and hence the device body, hosts the integrally-formed textured surface, with the structures being suitable for the establishment of a uniform biological layer thereupon. The obverse side may be a closed surface such as the inner blood-contacting surface of a tube or bladder. The dip-coating solution and wax device form can be removed from the vacuum chamber; the wax form can be removed from the solution at a controlled rate. Repeated coatings of polyurethane solution can be applied to the wax device form in this manner until a preselected wall thickness is achieved.

Figure 2I:
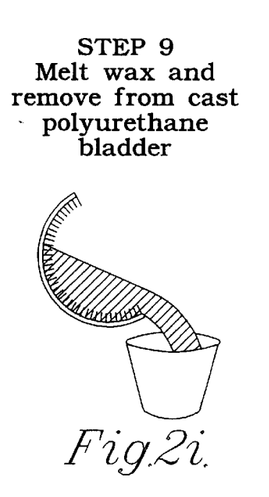
Figure 2J:
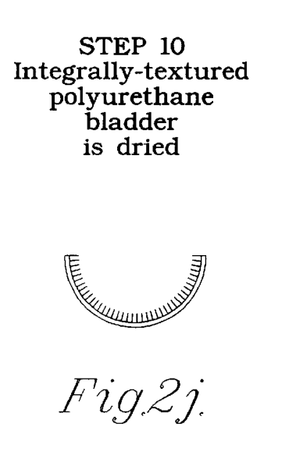

In FIG. 2i, the dissoluble wax device form can be melted out of the dip-coated polyurethane device by submerging the coated form in water that is heated to a temperature above the melting point of the wax. As the wax melts, it tends to flow out of the polyurethane device and float to the top of the water bath, where it can be collected. The wax removal can continue until water has replaced most of the wax. Some residual wax may remain on the fibrils of the integrally-textured surface. Therefore, the de-tooled polyurethane device can be placed in a container of solvent to dissolve and rinse away the residual wax. The solvents can include d-limonene and xylene, with d-limonine being preferred. The solvent bath is heated to a temperature less than the flash point of the solvent. A stirrer or other means of agitation, such as an ultrasonic bath, can be employed to increase the amount of solvent washing the surface of the textured polyurethane. The integrally-textured polyurethane implantable device can remain in the solvent for 4 to 24 hours, after which it is placed in a new bath containing clean solvent. The implantable device again can be soaked for between about 2 to about 24 hours and placed in a third bath of clean solvent for another 2 to 24 hours. The implantable device then can be rinsed repeatedly with an n-alcohol to remove residual solvent. Methanol, ethanol, propanol, and butanol can be used as the n-alcohol, with propanol being preferred. The polyurethane device can be drained of residual alcohol and rinsed with distilled water to remove traces of solvents. The polyurethane device can be dried in a vacuum oven at 60° C. to 90° C. under vacuum for 4 hours, as illustrated in FIG. 2j.

Figure 3:
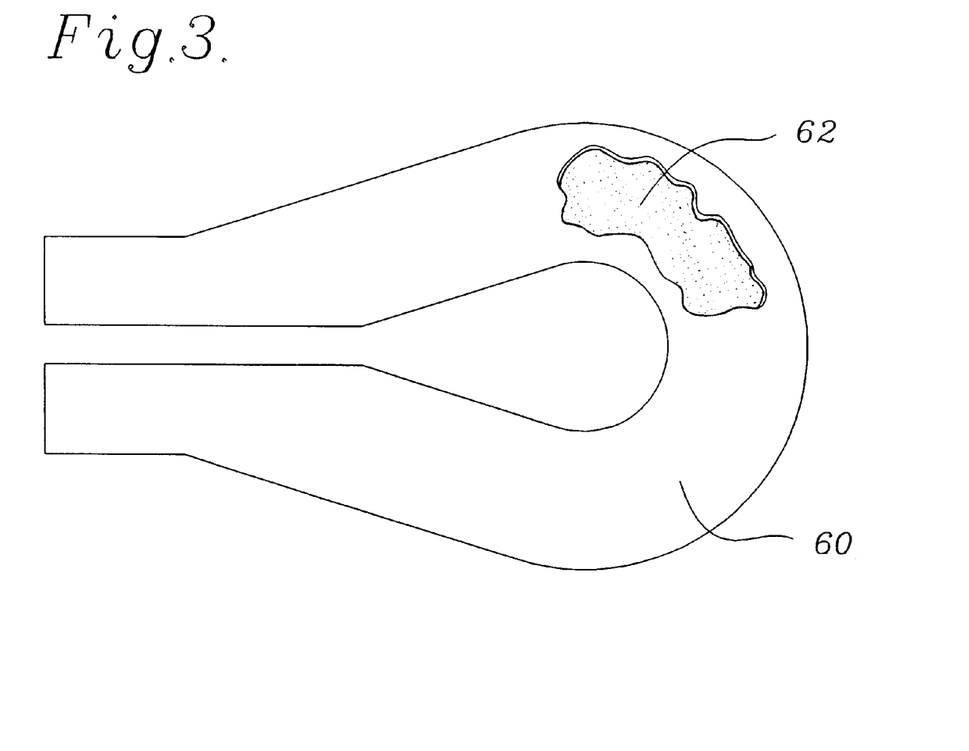
FIG. 3 is a diagram in partial section of an integrally-textured polyurethane blood bag that was produced by one embodiment of the invention herein.

One example of an implantable device having a complex shape and an integrally-textured, blood-contacting surface is blood conduit 60 which is U-shaped for use in an implanted aortic counter-pulsation device and is illustrated in FIG. 3.

Figure 4:
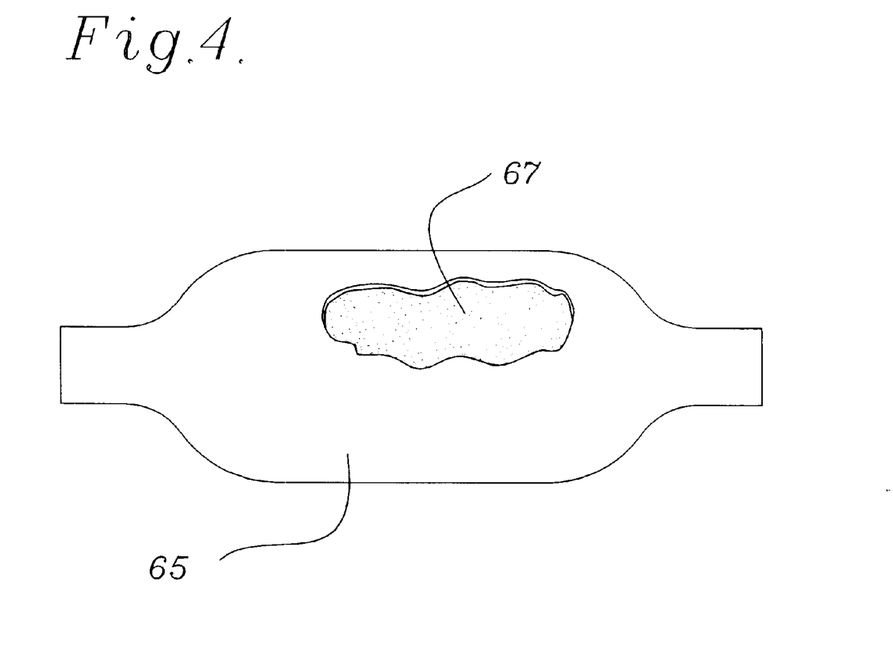
FIG. 4 is a diagram in partial section of an integrally-textured, U-shaped conduit for an aortic counter-pulsation device.

A portion of conduit 60 has been removed in FIG. 3, illustrating an integrally-textured inner surface 62 which is blood-compatible and upon which a generally uniform biological layer can be established. FIG. 4 is a diagram which shows the shape of finished blood bag 65 and illustrates one particular complex device geometry that can be produced by utilizing a method according to the present invention. A portion of blood bag 65 has been removed in FIG. 4, illustrating an integrally-textured inner surface 67 which, like surface 62 in FIG. 3, is blood-compatible and upon which a generally uniform biological layer can be established.

Figure 5:
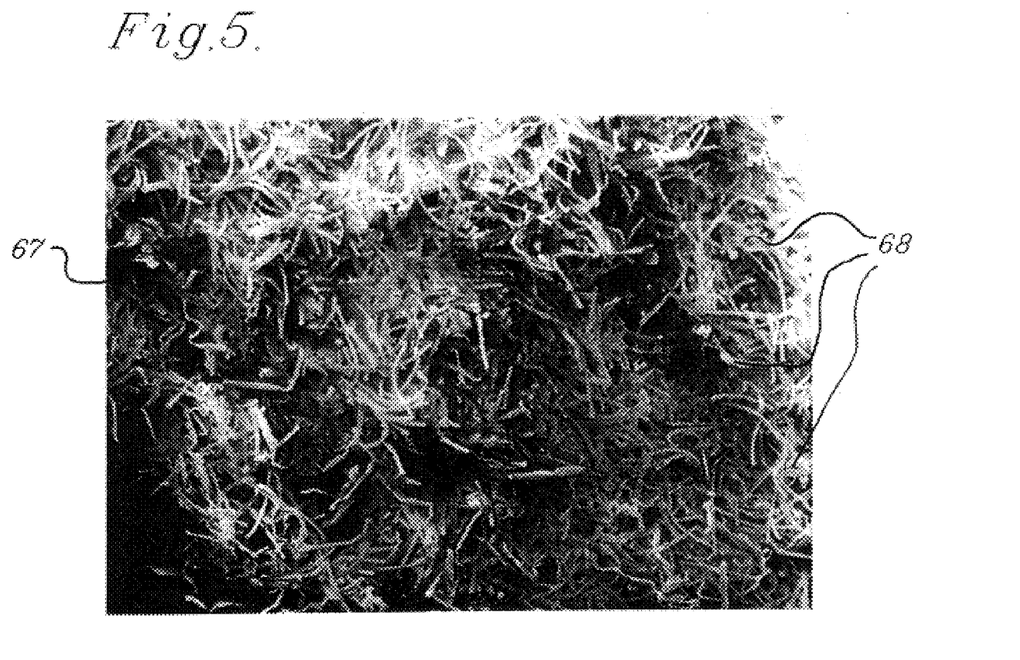
FIG. 5 is a scanning electron photomicrograph at 30X magnification of an integrally-textured polyurethane surface that was produced by one embodiment of the method according to the invention herein.
Figure 6:
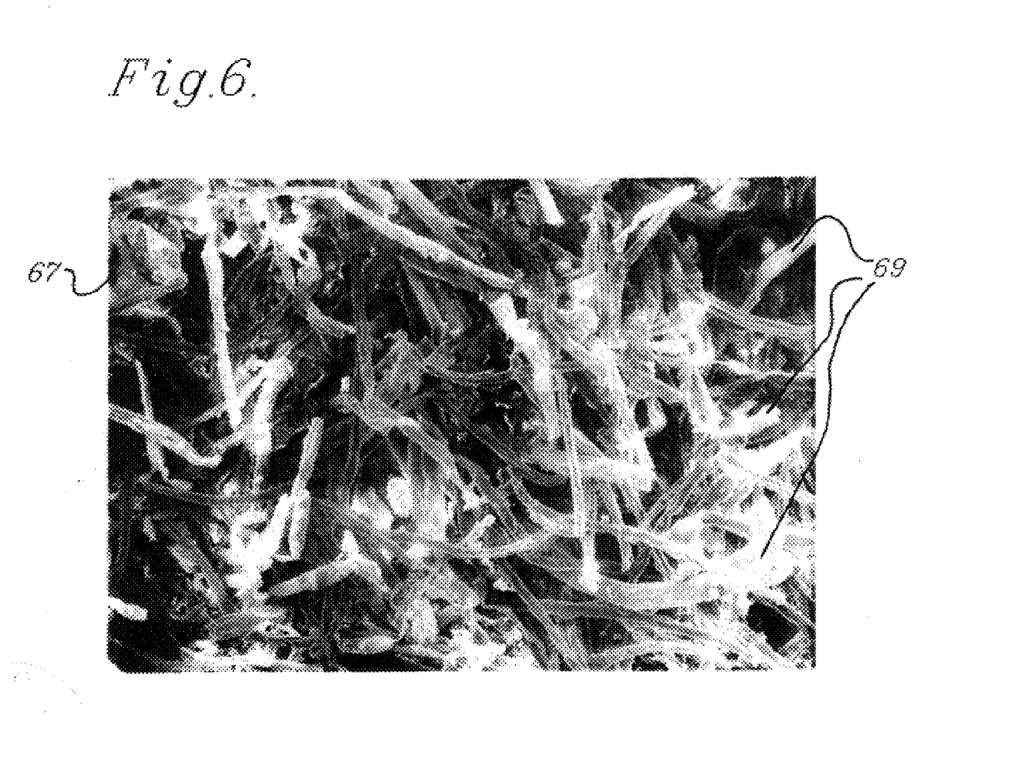
FIG. 6 is a scanning electron photomicrograph of the integrally-textured surface in FIG. 5 at 100X magnification.

Scanning electron photomicrographs of the resulting integrally-textured surface 67 of the blood bag in FIG. 4 are shown in FIG. 5 and FIG. 6. FIG. 5 is a 30 X magnification of a portion of surface 67 in FIG. 4 in which a plurality of integrally-formed structures, such as fibrils 68, can be seen. FIG. 6 is a 100X magnification of a portion of surface 67 in FIG. 4 in which a plurality of integrally-formed structures, such as fibrils 69, can be seen in greater detail than fibrils 68 in FIG. 5.

The device and method of the present invention are illustrated by way of the following example.

EXAMPLE

A silicone rubber mold for a blood bag was coated with an adhesive comprised of a solution of ethyl vinyl acetate in water having a solids content of about 46%-by-weight. The adhesive-coated surfaces were then flocked with about 3-denier-per-filament nylon fibers. The fibers had an average diameter of about 19 microns and average length of about 750 microns. The mating surfaces of the mold halves were cleaned of excess flock and flocking adhesive up to the edges of the mold cavity. The mold halves were assembled and the mold was placed in an oven at about 60° C. for about one hour to dry the flocking adhesive. The heated mold was removed form the oven and filled with melted beeswax that was heated to about 105° C. The wax-filled mold was allowed to cool in air for one hour and then the mold was opened and the wax device form was removed. The flocking adhesive that was on the outer surface of the wax form was softened with warm water and peeled away from the wax to expose the nylon flock.

The wax device form was placed in a stirred, unheated bath containing a mixture of 89% phenol and 11 water. The wax device form remained in the bath for about 96 hours to dissolve the nylon flock that was embedded in the beeswax form. The wax device form was removed from the phenol bath and rinsed repeatedly with acetone, and then water, to remove any residual phenol. The wax device form was air-dried and then dip-coated with a 15% solids solution of polycarbonate diisocyanate polyurethane in a dimethylacetamide solvent. A total of 5 coats of solution were put on the wax form. The first 3 dip-coats of the polyurethane solution were done under vacuum to remove any air entrapped in the surface of the beeswax form. Each coating of the polyurethane solution was dried at 50° C. in an oven for one hour. The beeswax form was melted out of the polyurethane blood bag by immersion in an 85° C. water bath for one hour. The polyurethane blood bag was then soaked in 3 different baths of d-limonine for 24 hours, 96 hours, and 24 hours respectively, to dissolve any residual beeswax. The polyurethane blood bag was then thoroughly rinsed with methanol to extract any residual solvents. The polyurethane blood bag was baked in a vacuum oven at 60° C. for 4 hours.

While certain presently preferred embodiments of the invention have been illustrated, it is understood that the invention is not limited thereto by may be otherwise variously embodied and practiced within the scope of the following claims.

I claim:

1. A method for producing an implantable device having an internal, closed blood-contacting surface and a complex shape, said complex shape being asymmetric, comprising the steps of:
   a. fabricating a mold having a complex shape corresponding to at least a portion of said implantable device;
   b. applying a flock to said mold;
   c. introducing a conformable dissoluble material to said mold, said flock being at least partially embedded in a dissoluble material surface of said dissoluble material adjacent to said mold;
   d. removing said dissoluble material having said embedded flock therein from said mold;
   e. removing said flock from said dissoluble material using a first solvent thereby creating a dissoluble device form having a form surface, said form surface corresponding to said dissoluble material surface and having a plurality of invaginations therein, said flock being substantially soluble in said first solvent and said dissoluble device form being substantially insoluble in said first solvent;
   f. applying a layer of a selected biologically stable device material to said dissoluble device form thereby forming a device wall thereon, said device material penetrating said plurality of invaginations of said form surface thereby forming a plurality of structures within respective ones of said plurality of invaginations, said device wall having said structures integrally formed thereon; and
   g. removing said dissoluble device form from said device wall and said structures thereon by liquefying said dissoluble device form thereby providing said implantable device.

2. The method of claim 1 wherein said applying a flock comprises the steps of:
   (a) applying an adhesive to at least a portion of said mold; and
   (b) removably imparting said flock to said at least a portion of said mold using a selected flock attaching technique.

3. The method of claim 2 wherein said flock is nylon.

4. The method of claim 3 wherein said first solvent includes phenol.

5. The method of claim 1 wherein said first solvent remains on said dissoluble material and wherein said removing said flock includes the step of removing said first solvent with a second solvent.

6. The method of claim 1 wherein said selected device material is at least partially dissolved to a first solids contents in a third solvent.

7. The method of claim 2 wherein said selected flock attaching technique includes electrostatically attaching said flock to said mold.

8. The method of claim 1 wherein removing said dissoluble device form further comprises the step of bathing said device form in a liquefacient, said liquefacient substantially liquefying said dissoluble device form.

9. The method of claim 8 wherein removing said dissoluble device form further comprises the step of bathing said implantable device in a fourth solvent, said fourth solvent dissolving a residual portion of said dissoluble device form.

10. The method of claim 1 further comprising the step of drying said implantable device at a drying temperature for a drying time, said drying following the step of removing said dissoluble device form.

11. The method of claim 1 wherein said conformable dissoluble material is a wax.

12. The method of claim 11 wherein removing said dissoluble device form further comprises the step of bathing said dissoluble device form in a liquefacient, said liquefacient substantially liquefying said wax.

13. The method of claim 12 wherein said liquefacient is water, said water having a temperature greater than the melting point of said wax.

14. The method of claim 12 further comprising the step of bathing said implantable device in a fourth solvent, said fourth solvent dissolving a residual portion of said wax.

15. The method of claim 6 wherein said selected device material is polyurethane.

16. The method of claim 15 wherein said third solvent is a polyurethane solvent.

17. The method of claim 16 wherein said polyurethane is polycarbonate diisocyanate polyurethane and said polyurethane solvent includes dimethylacetamide and dimethylformamide and tetrahydrafuran and 1,4-dioxane.

18. The method of claim 6 wherein said first solids content is between about 1% by weight to about 20% by weight.

19. The method of claim 18 wherein said first solids content is about 15% by weight.

20. The method of claim 1 wherein applying said layer of selected device material further includes the steps of:
   (a) dip-coating said dissoluble device form with a coating of device material; and
   (b) applying a vacuum to said dissoluble device form and said device material such that air entrapped in said invaginations is substantially evacuated therefrom.

21. The method of claim 20 wherein said vacuum is between about 5 psia to about 10 psia.

22. The method of claim 21 wherein said vacuum is repeatedly drawn and released.

23. The method of claim 20 wherein said layer is comprised of a plurality of coatings of said device material, said plurality of coatings providing said device wall with a predefined thickness.

24. The method of claim 23 further comprising the step of drying said device material between selected ones of said plurality of coatings.

25. The method of claim 4 wherein said first solvent is a mixture of phenol and water.

26. The method of claim 25 wherein the step of removing said flock includes the step of bathing said conformable dissoluble material in an agitated bath of said first solvent.

27. The method of claim 25 wherein said mixture includes about 89% phenol and about 11% water.

28. The method of claim 2 wherein said selected flock attaching technique includes the step of electrostatically attaching said flock to said mold.

29. The method of claim 28 wherein said adhesive is used in said electrostatic flock attaching technique.

30. The method of claim 29 wherein said adhesive is a water-based compound of ethyl vinyl acetate.

31. The method of claim 30 wherein said water-based compound has a solids content of less than about 60% by weight.

32. The method of claim 28 wherein said mold is substantially non-conductive and said selected flock attaching technique further includes the step of masking at least a portion of said mold with a conductive tape, said tape being substantially in contact with said adhesive, said mold becoming electrically conductive thereby.

33. The method of claim 2 wherein the step of applying said adhesive further comprises drying said adhesive before removably imparting said flock, said drying being at an adhesive drying temperature for an adhesive drying time.

34. The method of claim 33 wherein said adhesive drying temperature is between about 40° C. and about 90° C., and said adhesive drying time is generally at least one hour.

35. The method of claim 1 wherein the step of introducing said conformable dissoluble material includes soaking said mold and said conformable dissoluble material at an preselected casting temperature.

36. The method of claim 35 wherein said casting temperature is between about 60° C. and about 100° C.

37. The method of claim 14 wherein said fourth solvent is a wax-dissolving solvent.

38. The method of claim 37 wherein said wax-dissolving solvent is one of d-limonene and xylene.

39. The method of claim 9 wherein the step of removing said dissoluble device form further includes:
    (a) rinsing said implantable device in an n-alcohol, said rinsing substantially removing a residual solvent;
    (b) rinsing said implantable device in distilled water, said rinsing substantially removing a residual n-alcohol; and
    (c) drying said device at a drying temperature for a drying time.

40. The method of claim 33 wherein said adhesive drying temperature is between about 60° C. and about 90° C., and said adhesive drying time is generally at least one hour.

41. The method of claim 1 wherein said complex shape is not capable of being readily removed from said mold.

* * * * *